(12) United States Patent
Liu et al.

(10) Patent No.: US 11,445,992 B2
(45) Date of Patent: Sep. 20, 2022

(54) DEEP-LEARNING BASED SEPARATION METHOD OF A MIXTURE OF DUAL-TRACER SINGLE-ACQUISITION PET SIGNALS WITH EQUAL HALF-LIVES

(71) Applicant: ZHEJIANG UNIVERSITY, Hangzhou (CN)

(72) Inventors: Huafeng Liu, Hangzhou (CN); Jinmin Xu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 957 days.

(21) Appl. No.: 16/213,499

(22) Filed: Dec. 7, 2018

(65) Prior Publication Data
US 2020/0037974 A1 Feb. 6, 2020

(30) Foreign Application Priority Data
Aug. 2, 2018 (CN) .......................... 201810507876.3

(51) Int. Cl.
| | |
|---|---|
| *A61B 6/00* | (2006.01) |
| *G06N 20/00* | (2019.01) |
| *A61B 6/03* | (2006.01) |
| *G06N 7/08* | (2006.01) |
| *G06N 3/04* | (2006.01) |

(Continued)

(52) U.S. Cl.
CPC ............ *A61B 6/5205* (2013.01); *A61B 6/037* (2013.01); *G06N 3/0454* (2013.01); *G06N 7/08* (2013.01); *G06N 20/00* (2019.01); *G06T 7/0012* (2013.01); *G21H 5/02* (2013.01);
(Continued)

(58) Field of Classification Search
CPC ....... A61B 6/5205; A61B 6/037; A61B 6/486; A61B 6/5217; A61B 6/481; G06N 7/08; G06N 20/00; G06N 3/0481; G06N 3/0454; G06N 3/0445; G06N 3/088; G21H 5/02; G06T 7/0012; G06T 7/187;
(Continued)

(56) References Cited

U.S. PATENT DOCUMENTS

2008/0033291 A1* 2/2008 Rousso ................ A61B 5/416
600/436

FOREIGN PATENT DOCUMENTS

CN 107133997 * 9/2017

* cited by examiner

*Primary Examiner* — Amelie R Davis
(74) *Attorney, Agent, or Firm* — Jiwen Chen; Jacobson Holman PLLC

(57) ABSTRACT

The present invention discloses a DBN based separation method of a mixture of dual-tracer single-acquisition PET signals labelled with the same isotope. It predicts the two separate PET signals by establishing a complex mapping relationship between the dynamic mixed concentration distribution of the same isotope-labeled dual-tracer pairs and the two single radiotracer concentration images. Based on the compartment models and the Monte Carlo simulation, the present invention selects three sets of the same radionuclide-labeled tracer pairs as the objects and simulates the entire PET process from injection to scanning to generate enough training sets and testing sets. When inputting the testing sets into the constructed universal deep belief network trained by the training sets, the prediction results show that the two individual PET signals can been reconstructed well, which verifies the effectiveness of using the deep belief network to separate the dual-tracer PET signals labelled with the same isotope.

6 Claims, 3 Drawing Sheets

(51) Int. Cl.
*G06T 7/00* (2017.01)
*G21H 5/02* (2006.01)
(52) U.S. Cl.
CPC .............. *G06T 2207/10104* (2013.01); *G06T 2207/20081* (2013.01); *G06T 2207/20084* (2013.01)
(58) Field of Classification Search
CPC . G06T 2207/10104; G06T 2207/20081; G06T 2207/20084
See application file for complete search history.

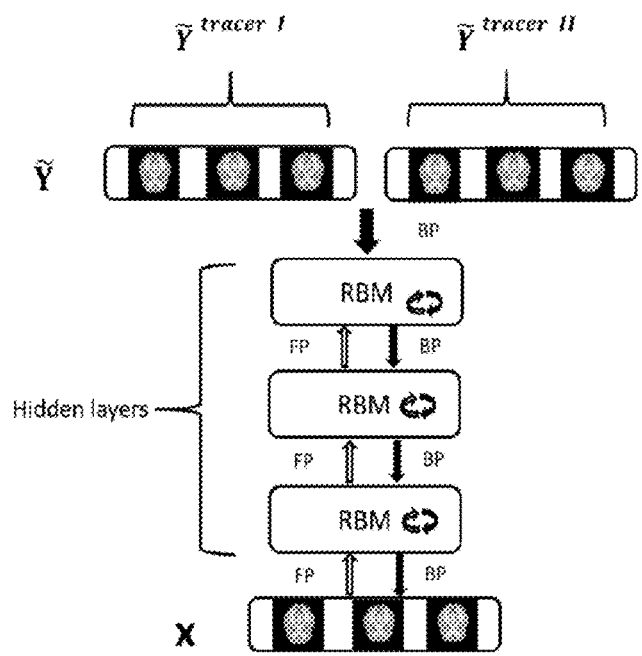
Fig.2
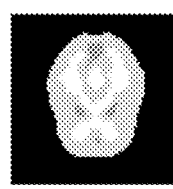  
Fig.3(a)　　　　Fig.3(b)　　　　Fig.3(c)
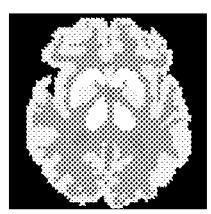 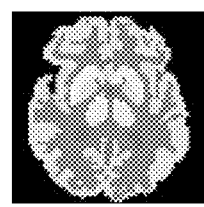 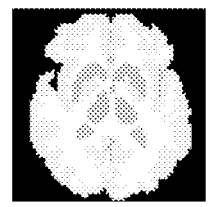 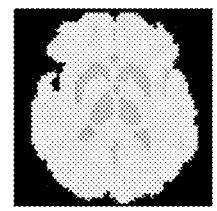
Fig.4(a)　　Fig.4(b)　　Fig.4(c)　　Fig.4 (d)

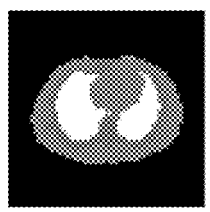 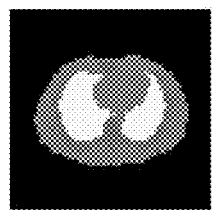 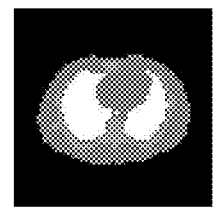 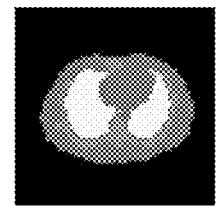
Fig.5(a)　　　Fig.5 (b)　　　Fig.5(c)　　　Fig.5(d)
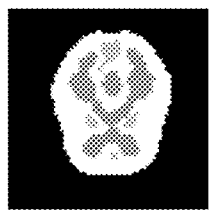 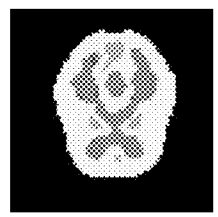 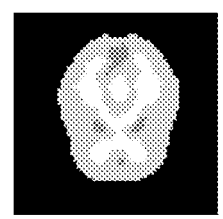 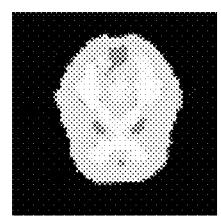
Fig.6(a)　　　Fig.6(b)　　　Fig.6(c)　　　Fig.6(d)

DEEP-LEARNING BASED SEPARATION METHOD OF A MIXTURE OF DUAL-TRACER SINGLE-ACQUISITION PET SIGNALS WITH EQUAL HALF-LIVES

This application claims the priority benefit of Chinese Application No. 201810507876.3, filed Aug. 2, 2018 in Chinese, which is hereby incorporated by reference.

FIELD OF TECHNOLOGY

The present invention belongs to the field of PET (positron emission tomography) imaging, which involves a dual-tracer PET separation method based on Deep Belief Networks (DBN) aiming at the tracer pairs labelled with the same isotope.

BACKGROUND TECHNOLOGY

Positron emission tomography (PET) is a kind of functional medical imaging modality used to detect the physiochemical activity in living bodies. The technology is often used to measure the physiological indexes (i.e. glucose metabolism, hypoxia, blood flow, and hypoxia) of the certain parts. The technology of imaging different functions in different parts in the living body mainly relies on various radioactive tracers. Researchers replaced one or more atoms in a chemical compound (i.e. Glucose, protein, nucleic acid) by a radionuclide ($^{11}$C, $^{13}$N, $^{15}$O, $^{18}$F is most common) to make radioactive tracers. By using bolus and continuous infusion protocols, the tracers will concentrate in a certain part in the living body that referred as Regions of Interest (ROIs), where it decays in a certain rate. During the decay period, it emits a positron, which travels a short distance before annihilating with an electron. This annihilation produces two high-energy (511 keV) γ photons propagating in nearly opposite directions. The two γ photons will be detected by detectors outside of the body, then the reconstruction algorithm will be performed to recover a radioactive concentration distribution image.

However, for a specific part of the body, multi-faceted, multi-angle detection can provide more information, and depicting the physiological and functional status of the tumor from different aspects also helps to improve the diagnostic accuracy, so the dual-tracer PET imaging is very necessary. In order to save scan time, reduce patient suffering and improve diagnostic efficiency, single-scan dual-tracer PET dynamic imaging has become a key technology to be solved. Since an annihilation reaction produces a pair of 511 ekV γ photons, it cannot be from the energy point of view to distinguish between the two tracers. At present, there are two main types of mainstream dual-tracer PET separation methods: (1) separation of reconstructed dual-tracer PET images; (2) integration of separation algorithm into the separation process of dual-tracer PET, and direct reconstruction of the concentration distribution of the two radiotracers. The first type of algorithm is essentially a signal separation problem, and the solution is relatively extensive. The second type of algorithm requires complex reconstruction algorithms to support, and the practicality is not strong. At present, the researchers mainly focus on the first type of algorithm.

The separation operation based on the mixed dual-tracer PET image mainly depends on the difference of the tracer half-life and kinetic parameters, combined with the compartment model to solve, and most of them need to be interlaced. Two tracers were injected to provide partial non-mixed single tracer information to facilitate modeling and separation, which lengthens the scanning process for the entire PET.

The dual tracers labeled with the same radioactive isotope play important roles for clinical use. For example, [$^{18}$F] FDG-[$^{18}$F]FLT is used for detecting cell proliferation, [$^{11}$C] FMZ-[$^{11}$C]DTBZ is used for measuring neurotransmitter system, [$^{62}$Cu]ATSM-[$^{62}$Cu]PTSM is used for observing blood flow and hypoxia. However, when dual tracers are labeled with the same isotope, the distinguishability of the two signals is diminished, and clinical requirements require simultaneous injection of two tracers to reduce scan time, which renders most algorithms ineffective. The separation of PET signals with the same isotope labeling has become a difficult problem to solve.

SUMMARY OF THE INVENTION

According to all described above, the present invention provides a DBN based separation method of a mixture of dual-tracer single-acquisition PET signals labelled with the same isotope. With the help of information exaction ability of deep learning, two individual PET volumetric images can be separated from a mixture of dual-tracer PET images.

A DBN based separation method of a mixture of dual-tracer single-acquisition PET signals labelled with the same isotope comprises the following steps:

(1) injecting the dual tracers labelled with the same isotope (tracer I and tracer II) to a biological tissue and performing dynamic PET imaging on the biological tissue, and obtaining the coincidence counting vector corresponding to different moments, then constituting dynamic coincidence counting sequence $S^{dual}$ that reflects the mixed dual-tracer distribution.

(2) injecting the individual tracer I and tracer II labelled with the same isotope to the biological tissue sequentially and performing two separate dynamic PET imaging on them respectively, then obtaining dynamic coincidence counting sequences, denoted as $S^{I}$ and $S^{II}$, that reflect the tracer I and tracer II distribution, respectively.

(3) using PET reconstruction algorithm to acquire dynamic PET image sequences $X^{Dual}$, $X^{I}$ and $X^{II}$, which correspond to the dynamic coincidence counting sequences $S^{dual}$, $S^{I}$ and $S^{II}$.

(4) repeating step (1)~(3) multiple times to generate enough sequences of dynamic PET images sequences $X^{Dual}$, $X^{I}$ and $X^{II}$, and dividing them into training datasets and testing datasets.

(5) extracting time activity curves (TACs) of each pixel from dynamic PET images sequences $X^{Dual}$, $X^{I}$ and $X^{II}$, using the TAC of $X^{Dual}$ as input and the TAC of the corresponding $X^{I}$ and $X^{II}$ as ground truth, training by deep belief network to obtain dual-tracer PET reconstruction model.

(6) inputting every TAC of any $X^{Dual}$ into the PET reconstruction model one by one, outputting the TAC of the corresponding $X^{I}$ and $X^{II}$, the reshaping the TAC to obtain dynamic PET image sequences $X_{test}^{I}$ and $X_{test}^{II}$ corresponding to tracer I and tracer II.

Furthermore, the method used to extract TACs from dynamic PET image sequences $X^{Dual}$, $X^{I}$ and $X^{II}$ in step (5) can be formulated as:

$$X^{dual} = [TAC_1^{dual}\ TAC_2^{dual}\ \ldots\ TAC_n^{dual}]^T$$

$$X^{I} = [TAC_1^{I}\ TAC_2^{I}\ \ldots\ TAC_n^{I}]^T$$

$$X^{II} = [TAC_1^{II}\ TAC_2^{II}\ \ldots\ TAC_n^{II}]^T$$

wherein $TAC_1^{dual} \sim TAC_n^{dual}$ are the TACs of the 1st-n-th pixels in the dynamic PET images sequence $X^{Dual}$, $TAC_1^I \sim TAC_n^I$ are the TACs of the 1st-n-th pixels in the dynamic PET images sequence $X^I$, $TAC_1^{II} \sim TAC_n^{II}$ are the TACs of the 1st-n-th pixels in the dynamic PET images sequence $X^{II}$, n represents the total pixels of the PET image, and T represents transposition.

Furthermore, the training process of DBN in the described step (5) can be detailed as follows:

5.1 initializing a DBN framework consisting of an input layer, hidden layers and an output layer, wherein the hidden layers are composed of three stacked Restricted Boltzmann Machines (RBMs);

5.2 initializing the parameters in the described DBN, which includes the number of nodes in hidden layers, the offset vector and the weight vector between layers, learning rate, activation function and the maximum number of iterations;

5.3 pre-training the stacked RBMs in the hidden layers;

5.4 transmitting the parameters obtained from pre-training to initialized DBN, and then inputting the TAC in the dynamic PET image sequence $X^{dual}$ one by one into the DBN, calculating the error function L between the output result and the corresponding ground truth and applying the gradient descent method to continuously update the parameters of the whole network until the error function L converges or the maximum number of iteration is reached then a trained PET reconstruction model can be acquired.

Furthermore, in step 5.3, the restricted Boltzmann machine in the hidden layer is pre-trained, that is, each restricted Boltzmann machine is composed of a display layer and a hidden layer, and by the contrast divergence algorithm, the weight of each layer will be updated until the hidden layer can accurately represent the features of the display layer and can reverse the display layer. Furthermore, the loss function L described in step 5.4 is as follows:

$$L = \|\widehat{TAC}_j^I - TAC_j^I\|_2^2 + \|\widehat{TAC}_j^{II} - TAC_j^{II}\|_2^2 + \zeta\|(\widehat{TAC}_j^I + \widehat{TAC}_j^{II}) - (TAC_j^I + TAC_j^{II})\|_2^2$$

wherein $TAC_j^I$ is the TAC of the j-th pixel in the dynamic PET image sequence $X^I$; $TAC_j^{II}$ is the TAC of the j-th pixel in the dynamic PET image sequence $X^{II}$; $\widehat{TAC}_j^I$ and $\widehat{TAC}_j^{II}$ represent the two output results correspond to those in $X^I$ and $X^{II}$ that obtained after the TAX of the j-th pixel in the dynamic PET image sequence $X^{dual}$ are substituted into the DBN; j is a natural number and $1 \leq j \leq n$, n is the total number of the PET images, $\|\ \|_2$ the L2 norm; $\zeta$ is a user defined constant.

Furthermore, in the step (6), the TAC of the j-th pixel of $X^{dual}$ in the test set is input into the dual-tracer PET reconstruction model, and the output of the pixel is $[\overline{TAC}_j^I\ \overline{TAC}_j^{II}]$ with respect to the two individual tracers, wherein $1 \leq j \leq n$, n is the total number of the PET images. According to the procedures above, the TAC of all the pixels of $X^{dual}$ are input to the model, then the dynamic PET image sequences $X_{test}^I$ and $X_{test}^{II}$ that correspond to tracer I and tracer II is obtained according to the following formula:

$$X_{test}^I = [\overline{TAC}_1^I\ \overline{TAC}_2^I\ \ldots\ \overline{TAC}_n^I]^T$$

$$X_{test}^{II} = [\overline{TAC}_1^{II}\ \overline{TAC}_2^{II}\ \ldots\ \overline{TAC}_n^{II}]^T$$

wherein T represents matrix transposition.

The present invention described above can achieve the separation of a mixture of dual-tracer single-acquisition PET signals labelled with the same isotope by the trained DBN framework. A point-to-point mapping relationship between a mixed dual-tracer PET image and two single-tracer PET images was learned by inputting training data and ground truth into the constructed neural network. It is worth mentioning that this network is universal. The training set contains multiple sets of tracer combinations labeled with the same isotope, and the results show the good performance of this model on dual-tracer separation.

In summary, the present invention includes a universal framework constructed by deep belief network to establish a mapping relationship for the separation of dual tracers. By the powerful feature extraction capabilities of it, the signal separation of dual-tracer PET with the same isotope can be achieved well

BRIEF DESCRIPTION OF THE DRAWINGS

FIG. 2 is the structure of the DBN according to the present invention.

FIG. 3(a) is the Hoffman brain template.

FIG. 3(b) is the complex brain template.

FIG. 3(c) is the Zubal thorax template.

FIG. 4(a) is the ground truth of $9^{th}$ frame of $[^{11}C]DTBZ$.

FIG. 4(b) is the estimated result of $9^{th}$ frame of $[^{11}C]DTBZ$.

FIG. 4(c) is the ground truth of $9^{th}$ frame of $[^{11}C]FMZ$.

FIG. 4(d) is the estimated result of $9^{th}$ frame of $[^{11}C]FMZ$.

FIG. 5(a) is the ground truth of $9^{th}$ frame of $[^{62}Cu]ATSM$.

FIG. 5(b) is the estimated result of $9^{th}$ frame of $[^{62}Cu]ATSM$.

FIG. 5(c) is the ground truth of $9^{th}$ frame of $[^{62}Cu]PTSM$.

FIG. 5(d) is the estimated result of $9^{th}$ frame of $[^{62}Cu]PTSM$.

FIG. 6(a) is the ground truth of $9^{th}$ frame of $[^{18}F]FDG$.

FIG. 6(b) is the estimated result of $9^{th}$ frame of $[^{18}F]FDG$.

FIG. 6(c) is the ground truth of $9^{th}$ frame of $[^{18}F]FLT$.

FIG. 6(d) is the estimated result of $9^{th}$ frame of $[^{18}F]FLT$.

SPECIFIC EMBODIMENTS OF THE INVENTION

Figure 1:
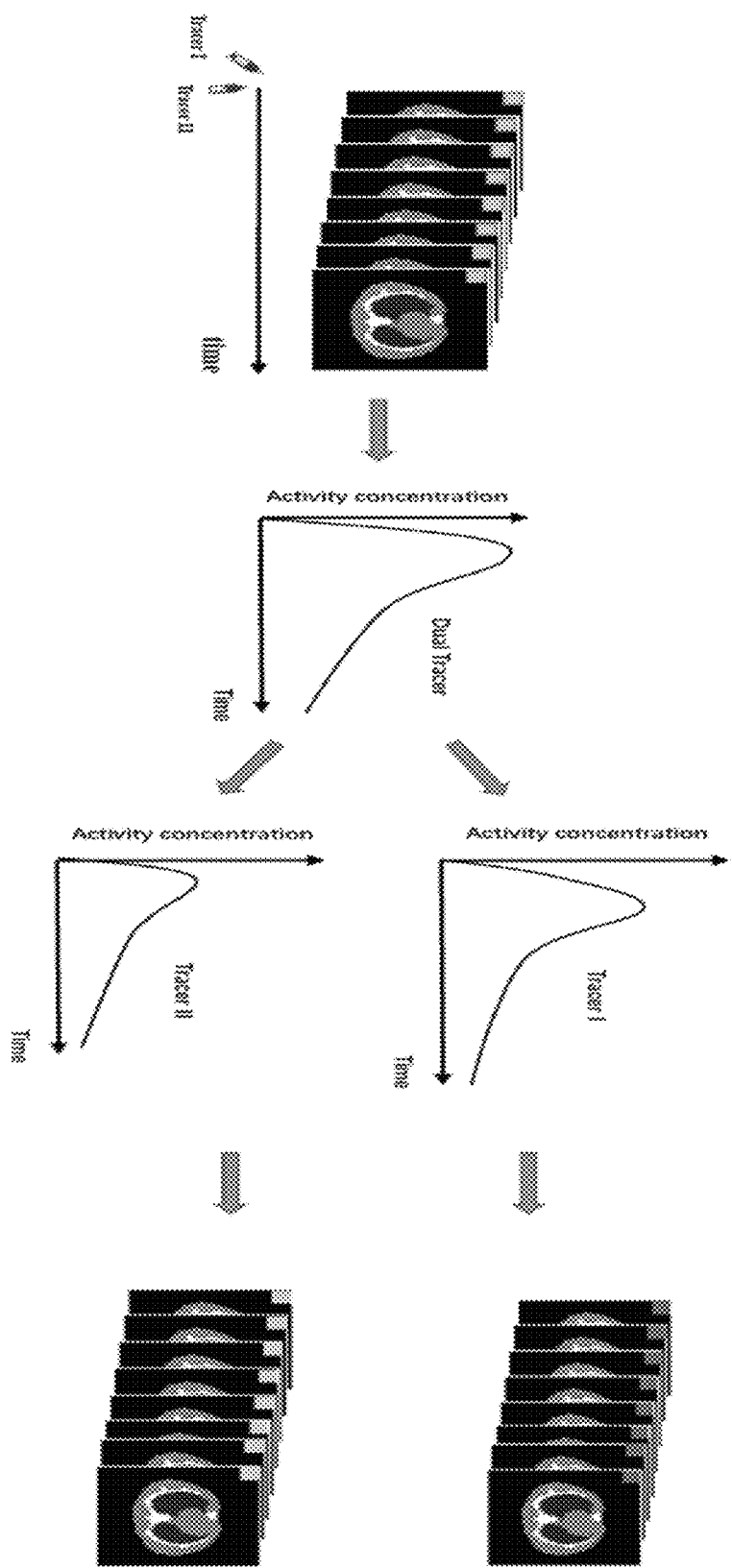
FIG. 1 is the flow diagram of the separation method of dual-tracer PET signals according to the present invention.

In order to more specifically describe the present invention, the detailed instructions are provided in conjunction with the attached figures and following specific embodiments:

As FIG. 1 shows, the present invention of DBN based separation method of a mixture of dual-tracer single-acquisition PET signals labelled with the same isotope include the following steps:

(1) Preparation of Training Data 1.1 Injecting the dual tracers labelled with the same isotope (tracer I and tracer II) to a biological tissue and performing dynamic PET imaging on it. Then a sequence of sinogram can be acquired, denoted as $S^{I+II}$.

1.2 Injecting the individual Tracer I and Tracer II labelled with the same isotope to the biological tissue sequentially and performing two separate dynamic PET imaging on them, respectively. Then two sequences of sinogram can be acquired, denoted as $S^I$ and $S^{II}$.

1.3 Using the reconstruction algorithm to reconstruct the sinogram to the concentration distribution of the radioactive tracer in the body, which are denoted as $X^{dual}$, $Y^I$ and $Y^{II}$ corresponding to $S^{dual}$, $S^I$ and $S^{II}$ respectively.

1.4 Repeating step (1)~(3) to generate enough sequences of dynamic PET images $U^{Dual}$, $U^I$ and $U^{II}$, and dividing them into training datasets $U_{train}^{dual}$, $U_{train}^I$ and $U_{train}^{II}$ and testing datasets $U_{test}^{dual}$, $U_{test}^I$ and $U_{test}^{II}$ randomly with a ratio of around 2:1.

Extracting pixel based time activity curves (TACs) from the reconstructed images $X^{dual}$, $Y^I$, $Y^{II}$, the process can be described as follows:

$$X^{dual}=[x_1,x_2,x_3,\ldots,x_N]^T, x_i=[x_i^1, x_i^2,\ldots,x_i^M]^T$$

$$Y^I=[(y^1)_1,(y^1)_2,\ldots,(y^1)_N]^T, (y^1)_i=[(y^1)_i^1,(y^1)_i^2,\ldots,(y^1)_i^M]^T$$

$$Y^{II}=[(y^2)_1,(y^2)_2,\ldots,(y^2)_N]^T, (y^2)_i=[(y^2)_i^1,(y^2)_i^2,\ldots,(y^2)_i^M]^T$$

wherein $x_i^j$ represents the radioactive concentration of pixel i at j-th frame, $(y^1)_i^j$ and $(y^2)_i^j$ represent the radiotracer concentration of pixel point i of Tracer I and Tracer II at j-th frame, respectively, and N is the total number of pixels of the resulting PET image, M is the total number of frames acquired by dynamic PET.

(2) Preparation of Training Sets and Test Set Data.

70% of the TAC data set $X^{dual}$ is extracted as the training set $X_{train}^{dual}$, and the remaining 30% is used as the testing set $X_{test}^{dual}$, and $Y^I$ and $Y^{II}$ corresponding to the training set and the test set are respectively connected in series as the labels of the training set and the ground truth of the testing set, which can be shown as follows:

$$Y_{train}=[Y_{train}^I, Y_{train}^{II}]$$

$$Y_{test}=[Y_{test}^I, Y_{test}^{II}]$$

(3) Constructing a deep belief network for the signal separation of the dual-tracer PET with the same isotope; as shown in FIG. 2, this deep belief network consists of an input layer, three hidden layers, and an output layer.

(4) The training set is input into this network for training. The training process is as follows:

4.1 Initializing the network; initializing the deep belief network, including the number of nodes of all the layers, initializing offset vectors and weight matrix, setting learning rate, activation function and the number of iterations.

4.2 Inputting the $X_{train}^{dual}$ into the network for training; the training process is divided into two parts: pre-training and fine-tuning.

4.2.1 Pre-training: The contrast divergence algorithm is required to keep updating the parameters of each restricted Boltzmann machine until all stacked restricted Boltzmann machines are trained well. In more detail, each restricted Boltzmann machine consists of a display layer and a hidden layer, using the contrast divergence algorithm to update the weights until the hidden layer accurately express the characteristics of the display layer and reverse the display layer.

4.2.2 Fine-tuning: The parameters obtained by pre-training are copied to a common neural network with the same structure. These parameters are used as the initial values of the neural network to participate in the final fine-tuning process. The error function L between $\widetilde{Y_{train}}$ and label $Y_{train}$ is calculated. Based on L, the gradient descent algorithm is used to update the weight matrix of the entire network until the iteration stops.

The error function L is as follows:

$$L=\|\widetilde{Y_{train}^I}-Y_{train}^I\|_2^2+\|\widetilde{Y_{train}^{II}}-Y_{train}^{II}\|_2^2-\gamma(\|\widetilde{Y_{train}^{II}}-Y_{train}^I\|_2^2+\|\widetilde{Y_{train}^I}-Y_{train}^{II}\|_2^2)$$

wherein, the first two reflect the error between the ground truth and the predicted value, while the latter two are the difference between the two tracer signals; $\gamma$ is a defined constant used to adjust the proportion of the latter two items in the loss function.

4.3 Adjusting the parameters of the whole network by the backpropagation algorithm. The error function is as follows:

$$\text{Loss}(\widehat{TAC}_j^I,\widehat{TAC}_j^{II})=\|\widehat{TAC}_j^I-TAC_j^I\|_2^2+\|\widehat{TAC}_j^{II}-TAC_j^{II}\|_2^2+\xi\|(\widehat{TAC}_j^I+\widehat{TAC}_j^{II})-(TAC_j^I+TAC_j^{II})\|_2^2$$

wherein $\widehat{TAC}_j^I$ and $\widehat{TAC}_j^{II}$ and are the prediction value of $TAC_j^I$ and $TAC_j^{II}$ by the DBN respectively, and $\xi$ is the weigh coefficient.

(5) Inputting the TACs of the test set data $X_{test}^{dual}$ into the trained neural network to obtain the separation signal of the dual-tracer PET labeled with the same isotope.

Next, we validate the present invention by simulated experiment.

(1) Phantom Selection

There are three different dual tracers in training datasets, and every group is equipped with a different phantom with different Regions of interest (ROIs), which indicates different biochemical environment. FIG. 3(a) is the Hoffman brain phantom with 3 ROIs for [$^{18}$F] FDG+[$^{18}$F] FLT; FIG. 3(b) is the complex brain phantom with 4 ROIs for [$^{11}$C] FMZ+[$^{11}$C] DTBZ; FIG. 3(c) is the Zubal thorax phantom with 3 ROIs for [$^{62}$Cu] ATSM+[$^{62}$Cu] PTSM.

(2) The Simulation of PET Concentration Distribution

The parallel compartment model was used to simulate the motion of dual tracers, and then the stable dual-tracer concentration distribution can be acquired by solving the dynamic ordinary differential equations (ODEs). The single compartment model based on kinetic parameters was used to simulate the motion of a single tracer in vivo, and then the stable single-tracer concentration distribution can be acquired by solving the dynamic ordinary differential equations (ODEs).

(3) The Simulation of PET Scanning Process

Computer Monte Carlo simulations were used to perform the dynamic dual-tracer PET scans with the help of software GATE. All simulations are based on the geometry of the full 3D whole body PET scanner SHR74000, designed by Nippon Kanematsu Photonics Co., Ltd. The PET scanner is designed with 6 rings and each ring has 48 detector blocks. Each detector block consists of a 16×16 array of lutetium yttrium orthosilicate (LYSO) crystals. The ring diameter of the scanner is 826 mm. When three groups of dual tracers and a single tracer concentration distribution map was input the Monte Carlo system, corresponding sinogram data were acquired.

(4) Reconstruction Process

The sinogram was reconstructed using the classical ML-EM reconstruction algorithm to obtain the concentration distribution of the simulated radiotracer pairs.

(5) Acquisition of TAC Curve;

TACs Based on pixel were obtained by recombining the concentration distribution matrix of the three groups of mixed radioactive concentration tracers in the body.

(6) Training Process;

the 70% TACs of three dual-tracer groups ([$^{18}$F] FDG+[$^{18}$F] FLT, [$^{11}$C] FMZ+[$^{11}$C] DTBZ and [$^{62}$Cu] ATSM+[$^{62}$Cu] PTSM) was inputted to the DBN as training data to do the pre-training. The TAC curve of a single tracer serves as a label to provide feedback for fine-tuning the entire network.

(7) Testing

The remaining 30% was used to evaluate the validity of the network.

FIG. 4(a) and FIG. 4(b) are the simulated radioactive concentration images of the 9th frame of [$^{11}$C] DTBZ and the predicted radioactive concentration images obtained by the trained DBN, respectively. FIG. 4(c) and FIG. 4(d) are the simulated radioactive concentration images of the 9th frame of [$^{11}$C] FMZ and the predicted radioactive concentration images obtained by the trained DBN, respectively. FIG. 5(a) and FIG. 5(b) are the simulated radioactive concentration images of the 9th frame of [$^{62}$Cu] PTSM and the predicted radioactive concentration images obtained by the trained DBN, respectively. FIG. 5(c) and FIG. 5(d) are the simulated radioactive concentration images of the 9th frame of [$^{62}$Cu] ATSM and the predicted radioactive concentration images obtained by the trained DBN, respectively. FIG. 6(a) and FIG. 6(b) are the simulated radioactive concentration images of the 9th frame of [$^{18}$F] FDG and the predicted radioactive concentration images obtained by the trained DBN, respectively. FIG. 6(c) and FIG. 6(d) are the simulated radioactive concentration images of the 9th frame of [$^{18}$F] FLT and the predicted radioactive concentration images obtained by the trained DBN, respectively.

Comparing the predicted image with the simulated ground truth, it can be found that the constructed deep belief network can separate the dual-tracer PET signal with the same isotope label well. This confirms the effectiveness of the deep belief network in feature extraction and signal separation, and also demonstrates that the method of the invention is effective in processing PET signals labeled with the same isotope.

The description of the specific instances is to facilitate ordinary technicians in the technical field to understand and apply the present invention. It is obvious that a person familiar with the technology in this field can easily modify the specific implementation mentioned above and apply the general principles described here into other instances without the creative Labor. Therefore, the present invention is not limited to the above instances. According to the disclosure of the present invention, the improvement and modification of the present invention will be all within the protection scope of the present invention.

The invention claimed is:

1. A deep belief network based method of separating a mixture of dual-tracer positron emission tomography (PET) signals from dual-tracers labelled with the same isotope, which comprises the following steps:
    (1) injecting the dual tracers, including tracer I and tracer II, labelled with the same isotope to a biological tissue and performing dynamic PET imaging on the biological tissue, then obtaining a coincidence counting vector corresponding to different moments, and then forming a dynamic coincidence counting sequence reflecting a concentration distribution of a mixture of the dual tracers, denoted as $S^{dual}$;
    (2) injecting individual tracer I and tracer II to the biological tissue sequentially and performing two separate dynamic PET image acquisitions on the biological tissue respectively, obtaining coincidence counting vectors of the two separate dynamic PET image acquisitions corresponding to different moments, and constituting the dynamic coincidence counting sequences that respectively reflect the distribution of tracer I and tracer II, denoted as $S^I$ and $S^{II}$;
    (3) using a PET reconstruction algorithm to reconstruct dynamic PET images $X^{dual}$, $X^I$ and $X^{II}$ corresponding to the dynamic coincidence counting sequences $S^{dual}$, $S^I$ and $S^{II}$;
    (4) repeating step (1)~(3) multiple times to generate a plurality of dynamic PET image sequences $X^{dual}$, $X^I$ and $X^{II}$ and dividing them into training sets and testing sets;
    (5) extracting the time activity curve (TAC) of each pixel from the dynamic PET image sequences $X^{dual}$, $X^I$ and $X^{II}$, taking the TACs of the training set $X^{dual}$ as the input sample, and the TACs of the corresponding $X^I$ and $X^{II}$ as the ground truth, then training them by the deep belief network to obtain a dual-tracer PET reconstruction model; and
    (6) inputting every TAC of any $X^{dual}$ in the test set into the PET reconstruction model one by one, and outputting the TACs corresponding to $X^I$ and $X^{II}$, and finally reconstructing the TACs to obtain dynamic PET images $X_{test}^I$ and $X_{test}^{II}$ corresponding to tracer I and tracer II.

2. The separation method described in claim 1, characterized that, in the step (5), the TAC of each pixel is extracted from the dynamic PET image sequences $X^{dual}$, $X^I$ and $X^{II}$ according to the following formula:

$$X^{dual} = [TAC_1^{dual}\ TAC_2^{dual}\ \ldots\ TAC_n^{dual}]^T$$

$$X^I = [TAC_1^I\ TAC_2^I\ \ldots\ TAC_n^I]^T$$

$$X^{II} = [TAC_1^{II}\ TAC_2^{II}\ \ldots\ TAC_n^{II}]^T$$

wherein: $TAC_1^{dual} \sim TAC_n^{dual}$ is the TAC of the 1st to nth pixels in the dynamic PET image sequence $X^{dual}$, $TAC_1^I \sim TAC_n^I$ is the TAC of the 1st to nth pixels in the dynamic PET image sequence $X^I$, and $TAC_1^{II} \sim TAC_n^{II}$ is the 1st to nth pixels in the dynamic PET image sequence $X^{II}$, n is the total number of pixels of the PET image, and T represents matrix transposition.

3. The separation method according to claim 1, characterized in that: the specific process of training in the step (5) by a deep belief network (DBN) is as follows:
    5.1 initializing the DBN framework consisting of an input layer, hidden layers and an output layer, wherein the hidden layers are composed of three stacked Restricted Boltzmann Machines (RBMs);
    5.2 initializing the parameters in the DBN, which include the number of nodes in hidden layers, the offset vector and the weight vector between layers, activation function and the maximum number of iterations;
    5.3 pre-training the stacked RBMs;
    5.4 passing the pre-trained parameters to the initialized deep belief network, and then substituting the TAC in the dynamic PET image sequence $X^{dual}$ into the DBN, calculating an error function L between the output result and the corresponding ground truth, continuously updating the parameters of the entire network according to a gradient descent method until the error function L converges or reaches the maximum number of iterations, thus completing the training to obtain the dual tracer PET reconstruction model.

4. The separation method described in claim 3, characterized in that: in step 5.3, the restricted Boltzmann machine in the hidden layer is pre-trained, that is, each restricted Boltzmann machine is composed of one display layer and one hidden layer, and the weight of the hidden layer and the display layer is continuously updated by the contrast divergence algorithm, until the hidden layer can accurately represent the characteristics of the display layer and reverse the display layer.

5. The separation method described in claim 3, characterized in that: the formula of the error function L in the step 5.4 is as follows:

$$L=\|\widehat{TAC}_j^I - TAC_j^I\|_2^2 + \|\widehat{TAC}_j^{II} - TAC_j^{II}\|_2^2 + \zeta\|(\widehat{TAC}_j^I + \widehat{TAC}_j^{II}) - (TAC_j^I + TAC_j^{II})\|_2^2$$

wherein $TAC_j^I$ is the TAC of the j-th pixel in the dynamic PET image sequence $X^I$; $TAC_j^{II}$ is the TAC of the j-th pixel in the dynamic PET image sequence $X^{II}$; $\widehat{TAC}_j^I$ and $\widehat{TAC}_j^{II}$ represent the two output TACs corresponding to $X^I$ and $X^{II}$ by feeding the TAC of the j-th pixel in the dynamic PET image sequence $X^{dual}$ into the DBN; j is a natural number and $1 \leq j \leq n$, n is the total number of the PET images; $\| \|_2$ is the L2 norm; and $\zeta$ is a defined constant.

6. The separation method described in claim 1, characterized in that: in the step (6), the TAC of a j-th pixel of $X^{dual}$ in the test set is input into the dual-tracer PET reconstruction model, and then $[\overline{TAC}_j^I \ \overline{TAC}_j^{II}]$ is output corresponding to the two separated tracers, wherein $1 \leq j \leq n$, n is the total pixel number of the PET images;

according to the above procedures, the TAC of all the pixels of $X^{dual}$ are tested, then the dynamic PET image sequences $X_{test}^I$ and $X_{test}^{II}$ that correspond to tracer I and tracer II are obtained according to the following formula:

$$X_{test}^I = [\overline{TAC}_1^I \ \overline{TAC}_2^I \ldots \overline{TAC}_n^I]^T$$

$$X_{test}^{II} = [\overline{TAC}_1^{II} \ \overline{TAC}_2^{II} \ldots \overline{TAC}_n^{II}]^T$$

wherein T represents matrix transposition.

* * * * *